(12) United States Patent
Smith et al.

(10) Patent No.: US 6,258,064 B1
(45) Date of Patent: Jul. 10, 2001

(54) HELICALLY ADVANCEABLE ENDOSCOPIC NEEDLE DEVICE

(75) Inventors: Kevin W. Smith, Coral Gables; Juergen A. Kortenbach, Miami Springs; Charles R. Slater, Fort Lauderdale, all of FL (US)

(73) Assignee: Syntheon, LLC, Miami, FL (US)

( * ) Notice: Subject to any disclaimer, the term of this patent is extended or adjusted under 35 U.S.C. 154(b) by 0 days.

(21) Appl. No.: 09/411,856

(22) Filed: Oct. 4, 1999

(51) Int. Cl.[7] .................................................. A61M 5/178
(52) U.S. Cl. .............................. 604/164.12; 604/165.02
(58) Field of Search .......................... 604/95.01, 117, 604/118, 164.12, 164.13, 165.02, 158, 163, 164.07, 264

(56) References Cited

U.S. PATENT DOCUMENTS

| | | |
|---|---|---|
| 4,763,667 | 8/1988 | Manzo . |
| 5,320,608 * | 6/1994 | Gerrone ...................... 604/164.12 X |
| 5,380,292 * | 1/1995 | Wilson ............................. 604/165.02 |
| 5,429,138 * | 7/1995 | Jamshidi ............................. 600/566 |
| 5,536,256 * | 7/1996 | Yoon ................................ 604/164.12 |
| 5,620,453 * | 4/1997 | Nallakrishnan ...................... 606/166 |
| 5,766,184 | 6/1998 | Matsuno et al. . |
| 5,807,309 * | 9/1998 | Lundquist et al. ..................... 604/22 |
| 5,919,199 * | 7/1999 | Mers Kelly et al. ................. 606/139 |
| 5,964,756 * | 10/1999 | McGaffigan et al. .............. 604/22 X |

* cited by examiner

Primary Examiner—Anhtuan T. Nguyen
(74) Attorney, Agent, or Firm—David P. Gordon; David S. Jacobson; Thomas A Gallagher

(57) ABSTRACT

An endoscopic needle device includes an outer sheath, an elongate shaft extending through the sheath, a needle rigidly attached to the distal end of the shaft, and a handle assembly having a housing coupled to the proximal end of the sheath and having a syringe port in fluid communication with the sheath and a knob rotatably coupled to the housing. Rotation of the knob relative to the housing causes rotation of the shaft relative to the sheath. The needle and the distal end of the sheath are mated by a threaded connection. As such, rotation of the knob relative to the housing causes precise longitudinal movement and extension of the needle relative to the distal end of the sheath. A set of intermeshing gears are provided between the knob and shaft which function to permit at most one rotation of the knob to cause complete extension and/or retraction of the needle. Furthermore, assemblies are provided with permit the shaft to accommodate movement of the needle relative to the sheath. Moreover, the position of the knob relative to the housing provides an indication of the extension of the needle. As such, the injection needle device of the invention permits controllable and calibrated rotation of the needle to within a few degrees, such that the needle device can be easily, reliably, and precisely operated to advance the needle.

49 Claims, 5 Drawing Sheets

HELICALLY ADVANCEABLE ENDOSCOPIC NEEDLE DEVICE

BACKGROUND OF THE INVENTION

1. Field of the Invention

This invention relates broadly to endoscopic instruments. More particularly, this invention relates to endoscopic injection needle devices.

2. State of the Art

An endoscopic injection needle device is inserted through a lumen of a flexible endoscope to inject fluids under endoscopic visualization in body structures such as the esophagus, the stomach, and the colon. For example, during a colonic polypectomy, it is customary to inject saline solution into the tissue surrounding and underlying a polyp in order to raise the polyp to facilitate excision of the polyp by means of an endoscopic forceps or snares. Visible dyes and radiological contrast dyes are sometimes injected to mark the location of areas explored endoscopically so that the structures can be located during subsequent procedures. Additionally, sclerosing agents are sometimes injected into vascular structures, such as esophageal varicoceles, in order to cause clotting and to necrose the tissue so that it can be resorbed by the body.

Typically, an injection needle device consists of a flexible inner tubing (or fluid conduit), usually made of polytetrafluoroethylene (PTFE), surrounded by a loose-fitting outer jacket made of PTFE, fluorinated ethylene propylene (FEP), or similar flexible plastic, a handle assembly at the proximal ends of the inner tubing and outer jacket for relative axial movement thereof, and a needle attached to the distal end of the inner tubing.

In practice, a physician grips the outer jacket of the injection needle device with one hand to introduce it through a sealing port on the endoscope handle which communicates with the working channel of the endoscope and to position the distal end of the device proximate the desired tissue at the distal end of the endoscope. With his or her other hand, the physician holds the proximal handle of the endoscope so that the steering knobs on the endoscope handle can be manipulated while viewing the endoscopic image. The handle assembly of the endoscopic needle device is held and manipulated by an assistant, according to the oral commands of the physician. The assistant moves one component of the handle assembly relative to the other to move the inner tubing axially relative to the outer jacket, thus retracting the needle into the outer jacket or extending it beyond the distal tip of the outer jacket. Once the needle is in position, the assistant then injects a fluid or medicament into the tissue by means of a syringe attached to the handle assembly of the device.

The amount of penetration of the needle into the tissue is not easily controlled by either the physician or the assistant. The depth of penetration of the needle is limited only by the fact that the fluid conduit (or the connector joining the needle point to the fluid conduit) which is larger in diameter than the needle, abuts the tissue. In an alternative procedural method, the physician pushes the jacket up against the tissue, and then the physician orders the assistant to fully advance the needle. In this manner, there is no visualization or degree of control to the penetration of the needle point, except as limited by the abutment of the fluid conduit or connector against the tissue. If the physician determines that a different amount of needle penetration is desired, another device with a needle point of a different length must be used.

While it is customary for a physician to standardize his practice with a needle of a certain penetration length, it sometimes is necessary to inject more superficially, to reduce the possibility of penetrating the tissue structure, or more deeply, to reach a plane of dissection to separate layers of tissue. Therefore, it is necessary to stock several injection needle devices in each gastroenterology suite, each device having a needle with a different length to accommodate the needs of the physician.

A few prior art devices have been built which allow the assistant to control the depth of needle projection beyond the distal end of the jacket, but these devices are imprecise and awkward. For example, the devices described in U.S. Pat. No. 5,380,292 to Wilson and U.S. Pat. No. 4,763,667 to Manzo attempt to achieve a measure of adjustability of the needle projection by utilizing an adjustable stop on the handle assembly of the device. The Wilson and Manzo devices do not have a calibrated control mechanism, and there is no way for the assistant to accurately adjust the depth of needle penetration while the device is in place in the endoscope, because such would require visualization of the needle point and measurement of its projection beyond the distal end of the jacket while turning an adjustment nut. Rather, the Wilson and Manzo devices simply provide a manner by which the device can be prepared prior to use for a specific amount of needle projection. Unfortunately, even the adjustable stop is of limited value, because the design of these prior art devices is such that the length of needle point projection beyond the jacket is highly variable despite the stop. In fact, the position of the needle is strongly influenced by the shape of the endoscope and by forces acting on the needle point. Depending on the degree to which the endoscope is flexed to negotiate the anatomy of the patient, the length of needle projection of most prior art devices is variable because of the various possible positions of the fluid conduit tubing within the loose-fitting outer jacket of the device. Thus, as the device is flexed, the needle point moves relative to the distal end of the jacket. Also, such designs which use a flexible plastic tube for the fluid conduit, are not amenable to precise control of the needle projection, because their needles will retract to some degree, typically a few millimeters, when forced against tissue. Thus, these devices do not teach a practicable means of controlling the length of needle projection while the device is being used.

U.S. Pat. No. 5,766,184 to Matsuno et al. describes another needle device having an outer tubular sheath, an inner tubular member extending through the outer tubular sheath and longitudinally and axially rotatably movable relative thereto, a shaft extending through the inner tubular member and coupled to the needle, a needle at the distal end of the inner tubular member, and a handle assembly including a knob which permits axial rotation of the shaft, and therefore the inner tubular member and needle, relative to the sheath. The needle and the distal end of the outer sheath are threadably connected. This threaded connection permits helical rotation of the inner tubular member relative to the outer tubular sheath to cause precise longitudinal movement of the needle relative to the distal end of the outer tubular sheath. Fluid is injectable through the inner tubular member and the needle into the patient. However, the device has severe drawbacks. First, it is generally desirable that the pitch of the threads be sufficiently small to permit the fine and precise adjustment of the extension of the needle, e.g., movement of the needle to within a half millimeter. Such fine adjustment requires that the pitch of the thread in the connection preferably be no more than a half millimeter. Yet, this requires that the inner tubular member be rotated a very large number of times relative to the outer tubular member in order to move the needle the required distance. For example, at a pitch of a quarter millimeter, the inner tubular member and outer tubular sheath would need to be completely rotated thirteen times relative to each other in order to effectuate a 6.5 millimeter movement of the needle. Such device operation is impractical for two reasons. First, it is impractical for the physician or assistant to keep count of how many times he or she has rotated the knob which causes the inner tubular member to rotate relative to the outer tubular member. However, keeping count is required as there is no other means by which to determine how far the needle has been extended. As such, absent reliance on the physician's or assistant's memory as to how may times the inner tubular member and outer tubular sheath have been rotated relative to each other, it is not possible to determine from the proximal end of the instrument the extension of the needle from the distal end of the instrument. Second, even if the physician or assistant could accurately keep count of the number of rotations, such repetitive rotational movement is uncomfortable, resulting in hand strain. Therefore, this needle device is undesirable to both the physician and the assistant. Second, the patent fails to adequately describe a handle assembly which can correctly accommodate axial movement of the shaft and inner tubular member relative to the outer sheath as the needle is helically advanced and retracted.

SUMMARY OF THE INVENTION

It is therefore an object of the invention to provide an endoscopic needle device having a proximal handle assembly which accurately indicates the extension of the needle from the distal end of the device.

It is another object of the invention to provide an endoscopic needle device which requires rotation of a control member one turn or less relative to the handle assembly in order to move the needle from a retracted position into a fully extended position.

It is a further object of the invention to provide an endoscopic needle device which may be conveniently and comfortably operated.

It is also an object of the invention to provide an endoscopic needle device in which the needle is precisely adjustable to deliver different depths of penetration of the needle point while the device is in use.

It is an additional object of the invention to provide an endoscopic needle device which precisely controls the position of the needle relative to the distal end of the jacket.

It is yet another object of the invention to provide an endoscopic needle device in which extension of the needle is not affected by such factors as compressibility of the tubular components and relative slack of coaxial push-pull elements.

It is yet a further object of the invention to provide an endoscopic needle device in which the needle will not inadvertently retract even when subject to substantial force placed on the tip of the needle point.

In accord with these objects, which will be discussed in detail below, an endoscopic needle device is provided which includes an outer sheath, an elongate shaft extending through the sheath, and a needle rigidly attached to the distal end of the shaft. According to one embodiment of the invention, the needle includes a proximal opening such that the hollow of the needle is in fluid communication with the sheath. A substantially fluid-tight seal is provided between the needle and the sheath. The device further includes a handle assembly having a housing coupled to the proximal end of the sheath and having a port and channel in fluid communication with the sheath, such that a syringe may be coupled to the port and operated to inject a fluid (injectate) which travels through the channel, sheath and needle. The handle assembly also includes a knob rotatably coupled to the housing and coupled to the proximal end of the shaft. Rotation of the knob relative to the housing causes rotation of the shaft, and therefore the needle, relative to the sheath. The needle and the distal end of the sheath are mated by a threaded connection. As such, rotation of the knob relative to the housing causes precise helical movement and extension (or retraction) of the needle relative to the distal end of the sheath.

According to another embodiment of the invention, the needle is coupled to both the distal end of the shaft and an inner tubular member extending through the sheath. The needle is in fluid communication with the inner tubular member. The handle assembly has a housing coupled to the proximal end of the sheath and a knob rotatably coupled to the housing and coupled to the proximal end of the shaft. The housing also has a port and a channel in fluid communication with the inner tubular member, such that a syringe may be coupled to the port and operated to inject a fluid which travels through the channel, the inner tubular member and the needle. Rotation of the knob relative to the housing causes rotation of the shaft, and therefore the inner tubular member and needle, relative to the sheath, and results in precise helical movement and axial extension (or retraction) of the needle relative to the distal end of the sheath.

In accord with a preferred aspect of the invention, a set of intermeshing gears is provided between the knob and shaft and function to permit at most one rotation of the knob to cause complete extension and/or retraction of the needle. Furthermore, assemblies are provided with permit the shaft in the first embodiment, and shaft and inner tubular member in the second embodiment, to accommodate movement of the needle relative to the sheath. Moreover, in each embodiment, the position of the knob relative to the housing provides an indication of the extension of the needle. As such, the injection needle device of the invention permits controllable and calibrated rotation of the needle to within a few degrees, such that the needle device can be easily, reliably, and precisely operated to advance the needle.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
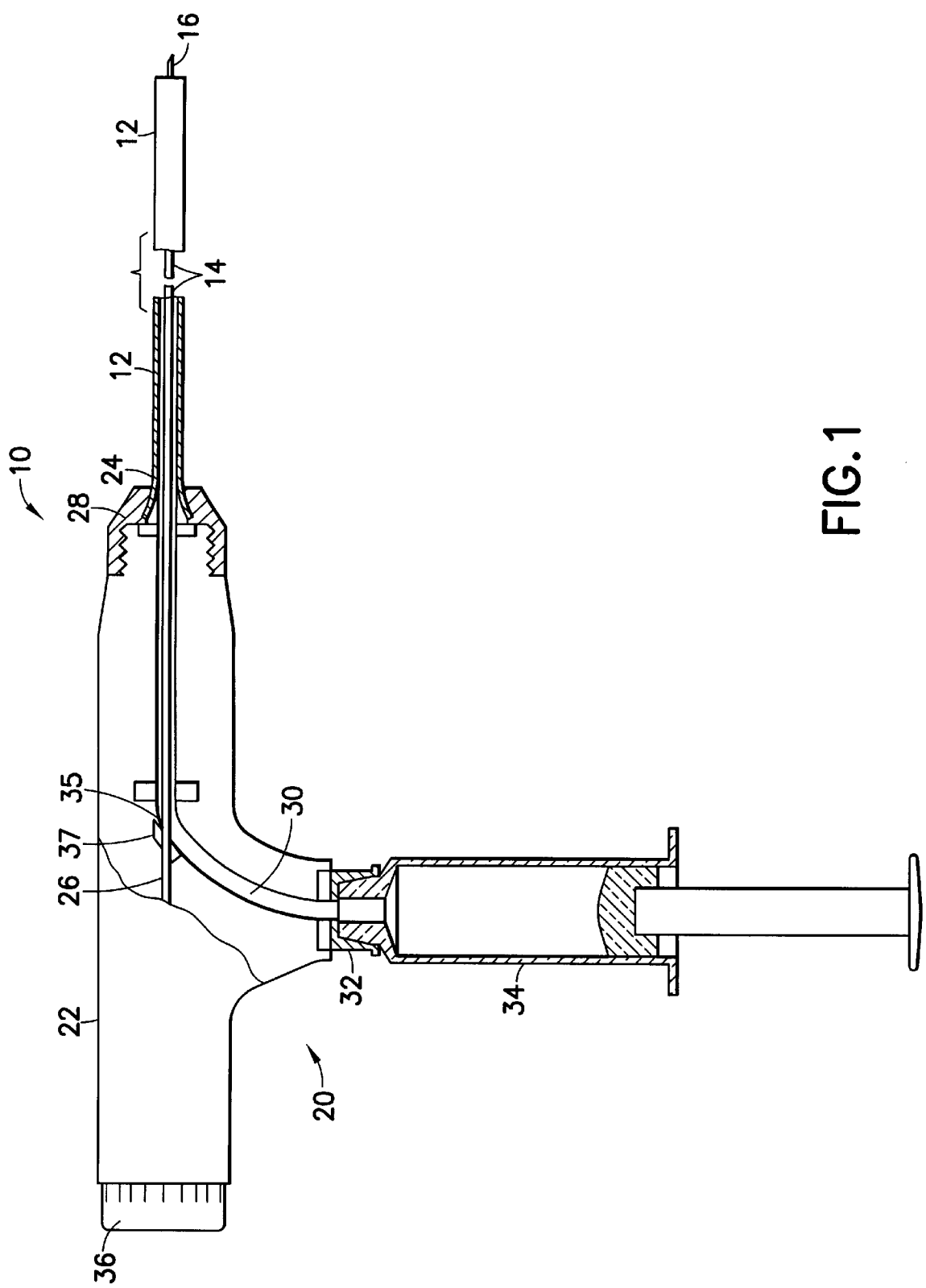
FIG. 1 is a broken partially cutaway side elevation of an endoscopic injection needle device according to the invention.
Figure 2:
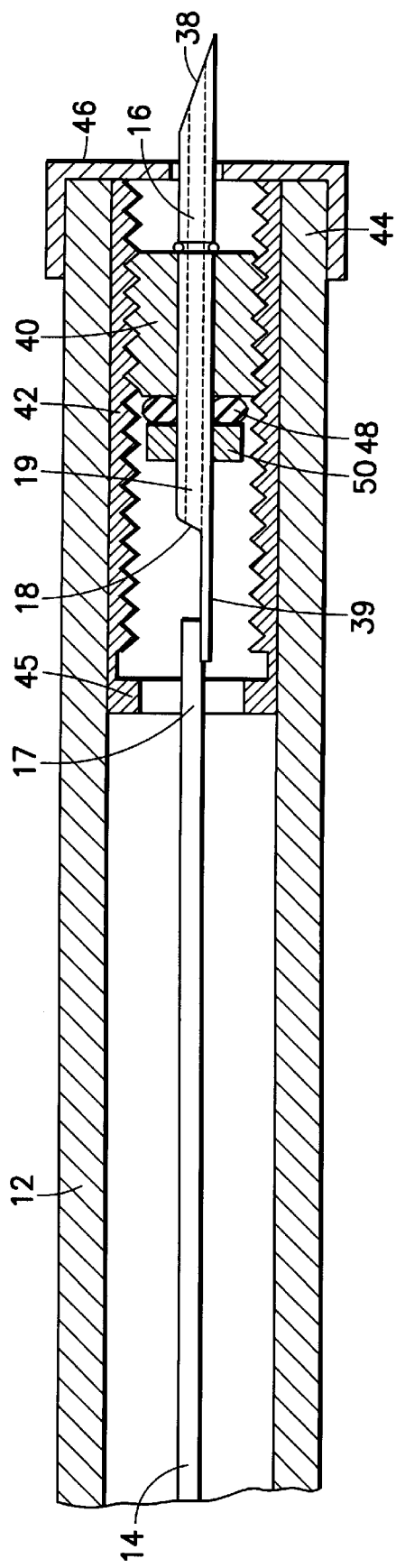
FIG. 2 is a longitudinal section view of a distal end of an endoscopic injection needle device according to the invention.

Turning now to FIGS. 1 and 2, an endoscopic injection needle device 10 includes a flexible tubular outer sheath 12, an elongate flexible shaft 14 extending through the sheath 12, and a needle 16 attached to a distal end 17 of the shaft 14. The needle 16 includes a proximal entryway 18 such that a bore 19 of the needle is in fluid communication with the sheath 12. A handle assembly 20 includes a housing 22 provided at the proximal ends 24, 26 of the sheath 12 and shaft 14. The proximal end 24 of the sheath 12 is coupled to the housing 22, preferably with a flare nut connection 28. The handle assembly 20 also includes a control knob 36 which is rotatably coupled to the housing 22. As will be discussed in detail hereinafter with respect to FIG. 3, rotation of the control knob 36 relative to the housing 22 causes rotation of the shaft 14 relative to the sheath 12. The housing 22 includes a channel or tube 30 having a syringe port, e.g., a female luer connection, in fluid communication with the sheath, such that a syringe 34 may be coupled to the port and operated to inject an injectate through the channel 30 and the sheath 12 (around shaft 14) and into the needle 16. The shaft 14 extends through the proximal end 24 of the sheath 12, into the channel 30, and exits through a hole or port 35 in the channel 30 and is coupled to the control knob 36. A substantially fluid-tight seal 37 is provided at the hole 35 to prevent fluid leakage therethrough.

The sheath 12 is preferably a length of PTFE tubing, and provides flexibility, sufficient strength to resist internal fluid pressure, and inertness to all known injectates. By way of example, the sheath 12 may be extruded PTFE tubing with an outside diameter of 0.078 inches and an inner diameter of 0.055 inches.

The shaft 14 is preferably a high strength, straightened (camber-free) stainless steel wire which extends continuously from the needle 16 to the handle assembly 20. The camber-free shaft 14 has a high elastic limit, and may be bent with the needle device through a tortuous path without permanent deformation. Moreover, as the shaft 14 is free of camber, rotation thereof precisely rotates the needle. By way of example, the shaft 14 may be 304V spring-temper wire of 325,000 psi UTS and 0.017 inch diameter.

Referring to FIG. 2, the needle 16 is preferably made from stainless steel tubing, preferably 25 gage, and preferably has a standard double-bevel needle point grind at its distal end 38. The proximal end of the needle is cut away to form a tab 39, which is attached to the distal end 17 of the shaft, and the entryway 18 allows the injectate fluid to enter the needle bore 19. Alternatively, the needle may be attached to the shaft with a crimp or by bonding, so long as an entryway is provided for fluid passage into the needle bore 19. If desired, the entryway may constitute a series of lateral holes in the needle.

Still referring to FIG. 2, the needle 16 has a threaded or helically-splined outer sleeve (needle sleeve) 40 crimped or bonded onto it, which in turn is engaged inside a threaded inner sleeve (sheath sleeve) 42 attached to or integral with the distal end 44 of the flexible tubular sheath 12. The needle 16 and distal end 44 of the sheath are thereby threadably connected. As the needle 16 is rotated, the needle sleeve 40 is induced to move helically through the sheath sleeve 42, so the needle 16 is advanced out of and retracted back into the distal end 44 of the sheath 12. The sheath sleeve 42 is preferably provided with an inwardly-directed lip 45 which functions as a stop to prevent retraction of the needle 16 beyond a maximum desirable amount. An end cap 46 is preferably provided at the distal end 44 of the sheath and functions as a stop to prevent extension of the needle beyond a maximum desirable amount. The threaded connection of the needle and sheath are also preferably provided with an O-ring 48 (or other resilient seal member) and a seal locking member 50 which prevents migration of the O-ring 48 along the needle 16. The O-ring 48 and seal locking member 50 together substantially prevent fluid traveling through the sheath 12 from exiting the distal end 44 of the sheath other than through the bore 19 of the needle 16. Alternatively or additionally, a fluid tight seal can be provided at the end cap 46 or proximal the sheath sleeve 42.

Figure 4:
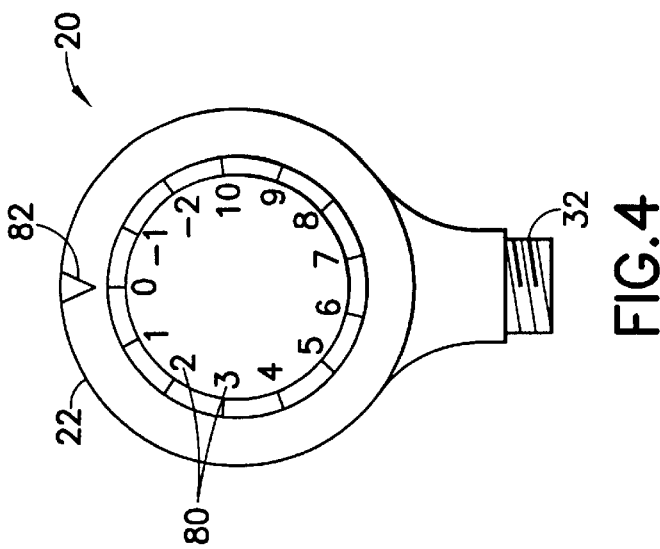
FIG. 4 is a proximal end view of the handle assembly of the injection needle device according to the invention, shown without a syringe coupled to the syringe port.
Figure 3:
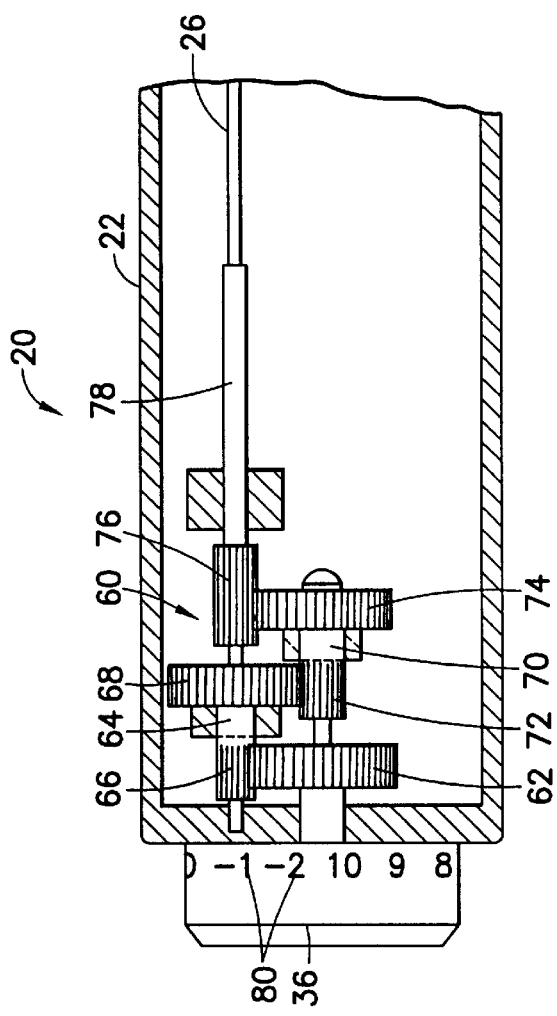
FIG. 3 is a broken section view of the handle assembly of an endoscopic injection needle device according to the invention.

Referring to FIGS. 3 and 4, the handle assembly 20 includes a "rotational step-up" means 60 so that the operator of the device is not required to rotate the control knob 36 more than one turn in order to extend or retract the needle a desired distance. For example, the threaded needle and sheath sleeves 40, 42 at the needle 16 and distal end 44 of the sheath, which generate the longitudinal movement of the needle in response to rotation of the shaft 14, may have a pitch in the range of 0.1 to 1.0 millimeter per turn, and preferably about 0.25 millimeters. Most physicians require needle extensions of eight millimeters or less, and it is desirable to have the needle retracted about two millimeters when not in use. As such, a total range of motion of at least ten millimeters is preferred. Thus, for threads with a 0.25 millimeter pitch, movement of the needle from a retracted position to that of greatest extension would require a total of forty turns. As discussed above in the background section, this is undesirable. According to a preferred aspect of the invention, the operator is only required to turn the control knob 36 of the handle assembly 20 at most one full turn, and preferably less than one full turn, to achieve the full range of motion (i.e., from a retracted position to a fully extended position). This aspect is achieved by the use of a rotational step-up means, preferably providing a rotational step-up ratio of about 1:50.

According to a preferred embodiment, the rotational step-up means 60 is a gear box of either spur-gear or planetary design. For example, a spur-gear box consisting of three increasing stages (1:4, 1:4, 1:3) provides a 1:48 ratio. According to the example, the control knob 36 includes a wheel 62 of forty teeth driving a change gear 64 with a pinion 66 of ten teeth and an output wheel 68 of forty teeth. The output wheel 68 of the change gear 64 drives a second change gear 70 with a ten tooth pinion 72 and thirty tooth wheel 74. The thirty tooth wheel 74 of the second change gear 70 drives a pinion 76 of ten teeth which includes a tubular output end 78 which is preferably coupled in an axially compliant manner, as described below, to the proximal end 26 of the flexible shaft 14. Thus, whenever the control knob 36 is rotated one turn, the flexible shaft 14 is rotated forty eight turns.

For a needle sleeve 40 having threads with 0.25 millimeter pitch, one full turn of the control knob 36 results in the needle 16 advancing, or retracting, twelve millimeters (forty eight turns×0.25 mm/turn), which provides more than the required minimum axial movement. For each millimeter of needle motion, the control knob 36 is turned thirty degrees (360 degrees/turn divided by 12 mm/turn). Thus, the control knob 36 is preferably calibrated in millimeter increments from −2 to 10, with the increments provided as indicia 80 on the control knob 36, each one millimeter increment preferably being thirty degrees from the next. An index mark 82 is provided on the housing 22 against which the incremental indicia 80 on the control knob 36 can be aligned or otherwise related to determine the exact position of the needle 16.

Alternatively, a faster pitch thread may be used on the needle sleeve 40. For example, using a one millimeter pitch, the shaft 14 need only be rotated ten times to achieve the desired motion. Thus, a 1:12 step-up ratio would suffice, which may be achieved with a relatively simpler gearbox: for example, two stages of 1:3 and 1:4. Even longer pitches could be used, but at pitches substantially longer than one millimeter the position of the needle 16 could be influenced by forces acting on the needle tip 38; that is, axial forces on the needle tip may cause the needle 16 to rotate and retract. Furthermore, a long-pitch thread results in lower mechanical advantage in the system, so that the advancement of the needle is not as reliable when the needle must be forced into tissue. This problem results from the very high torque that is required to generate penetration force at the needle, resulting in "wind-up" of the shaft.

As another alternative, shorter pitch threads, e.g, 0.1 millimeters, may be used, but such very fine threads are more fragile than the preferred moderate pitch threads, and also require greater precision in manufacture and assembly. Also, with shorter pitch threads, the required step-up means must have a very high ratio (e.g., 1:100), resulting in increased backlash and friction, which would in turn adversely affect the precision of needle advancement.

Thus, it can be seen that a moderate pitch thread, e.g., having a pitch of 0.25 mm, is most advantageous since such a thread permits the use of a practicable gear box, yet generates sufficient penetration force at the needle tip.

Figure 6:
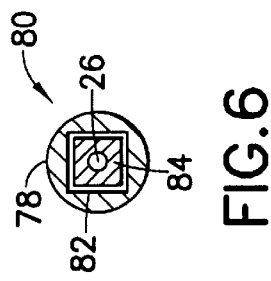
FIG. 6 is a section view across line 6—6 in FIG. 5.
Figure 5:
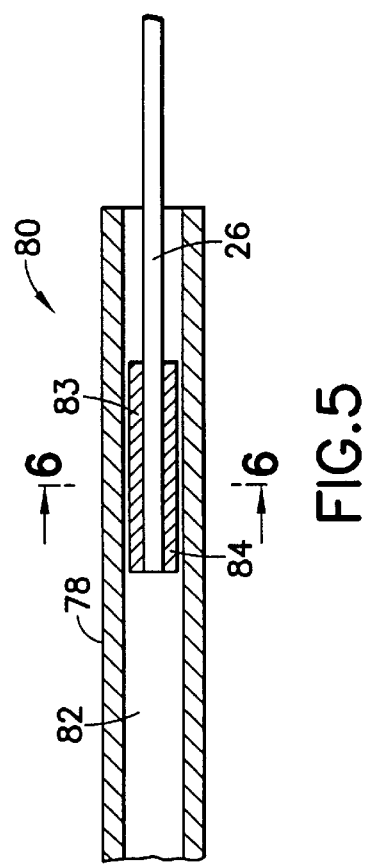
FIG. 5 is an enlarged broken section view of an axially-compliant joint for the connection between a handle assembly and a shaft of an injection needle device according to the invention.

Turning to FIGS. 5 and 6, regardless of which needle pitch is used, because rotation of the shaft causes the needle point to be translated proximally and distally, and because the control knob 36 is fixed axially to the housing 22, the proximal end 26 of the flexible shaft 14 is coupled to the output end 78 of pinion 76 in a manner which allows for the shaft to accommodate axial movement of the shaft. A preferred manner to achieve this axially-compliant coupling is with a sliding joint assembly 80. For the sliding joint assembly 80, the tubular output end 78 of the pinion 76 includes a non-circular bore 82, e.g., square or hexagonal in cross-sectional shape, and the proximal end 26 of the flexible shaft 14 is provided with an outer sleeve 83 defining a non-circular key 84, adapted to be received into and mate with the non-circular bore 82. Since only ten millimeters of longitudinal motion need be accommodated by the sliding joint assembly 80, a one millimeter square key approximately four millimeters in length can be received into a tubular output end 78 having a bore 82 approximately fifteen millimeters in length and of a square cross-section only slightly larger in size than the cross-sectional size of the key 84. The fifteen millimeter length of the bore accommodates greater manufacturing tolerances. As such, when the needle 16 is moved axially at the distal end of the device 10, the proximal end 26 of the flexible shaft 14 is permitted to slide within the bore 82 of the tubular output end 78 of the output pinion 76 to accommodate that axial movement. Therefore, the sliding joint assembly 80 maintains the ability to rotate the shaft 14 relative to the housing 22 and the sheath 12, even when the shaft 14 is moved axially relative to the housing 22 and sheath 12.

As a result, a single operator of the device, whether physician or assistant, can rotate the control knob 36 relative to the housing 22 and cause precise longitudinal movement and extension of the needle 16 relative to the distal end 44 of the sheath 12. The distance of longitudinal movement is indicated at the handle assembly 20 by the indicia 80, 82. The endoscopic injection needle device 10 precisely controls advancement of a needle to within a small fraction of a millimeter. In addition, the same operator can also inject fluid from within the syringe through the sheath and needle and into the tissue where the extended needle is located.

Figure 7:
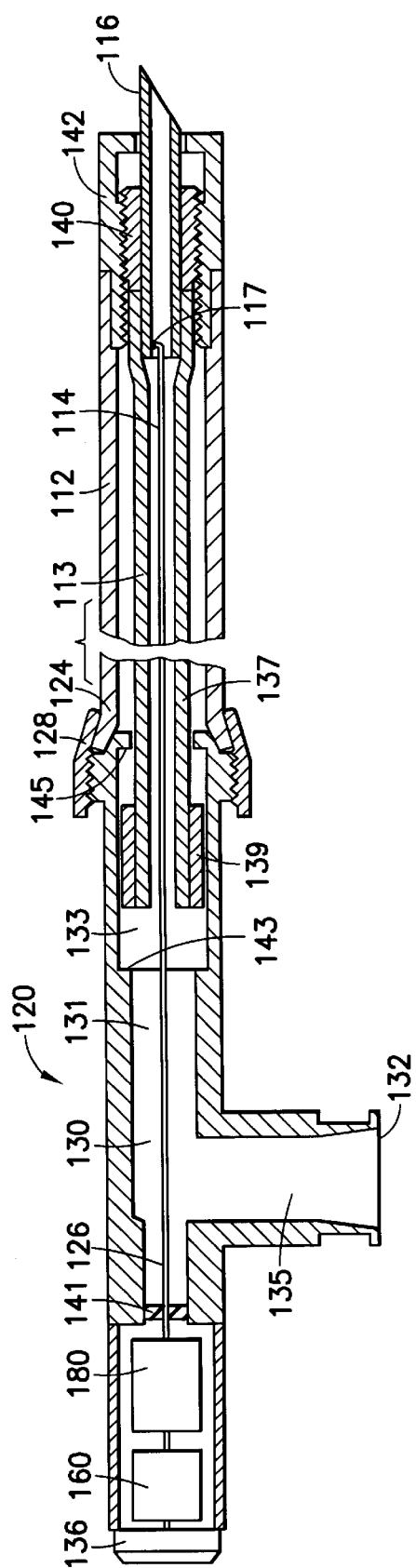
FIG. 7 is a broken side elevation section view of a second embodiment of an endoscopic needle injection device according to the invention.

Referring now to FIG. 7, a second embodiment of an endoscopic needle injection device, substantially similar to the first embodiment (with like parts having numbers incremented by 100) is shown. The device 110 includes a sheath 112, an inner tubular member 113 having a needle 116 at the distal end thereof and in fluid communication therewith, a flexible shaft 114 extending through the inner tubular member 113 and rigidly coupled to the needle 116, e.g., via a weld 117, and a handle assembly 120 for rotating the shaft 114 relative to the sheath 112. A threaded connection comprising a needle sleeve 140 about the needle 116, and a threaded cap 142 at the distal end of the sheath 112 is provided to permit helical rotation of the needle 116 relative to the sheath 112 to result in axial movement of the needle relative to the sheath. Rotation of the shaft 114 relative to the sheath causes rotation of the inner tubular member 113 and needle 116 relative to the sheath.

The handle assembly 120 includes a housing 122, and the proximal end 124 of the sheath 112 is coupled to the distal end of the housing with a flare nut connection 128. The housing 122 includes a T-shaped channel 130 having a first portion 131 aligned with the sheath and having a relatively enlarged diameter cavity 133 at the distal end of the housing and a second portion 135 terminating in a syringe port 132; i.e., a female luer lock. The proximal end 137 of the inner tubular member 113 is optionally provided with a ferrule 139 which is sized to axially slide and rotate within the cavity 133 (and provide a fluid seal), but yet is unable to exit the cavity due to stops 143 and 145. The ferrule 139 is preferably able to slide ten to twelve millimeters; i.e., a distance permitting the entire desirable range of axial movement of the needle. The proximal end 126 of the flexible shaft 114 extends through the first portion 131 of the bore 130 and through a substantially fluid-tight seal 141 to a sliding assembly 180, substantially as described above with respect to sliding assembly 80 in the first embodiment. The sliding assembly is further coupled to a gear assembly 160, substantially as described above with respect to gear assembly 60 in the first embodiment. The gear assembly 60 is coupled to a control knob 136.

In use, when the control knob 136 is rotated relative to the housing 122, the gear assembly 160 operates, as a described above, to step-up the rotation of shaft 114 rotation. As the shaft 114 rotates, the needle sleeve 140 on the needle 116 is rotated relative to the threaded end cap 142 at the distal end of the sheath 112, and the needle helically advances (or helically retracts when the knob is rotated in an opposite direction). A syringe (not shown) coupled to the syringe port 132 may be operated to inject fluid through the channel 130, the inner tubular member 113 and needle 116, without the use of substantially fluid-tight seals at the distal end of the instrument 110.

Figure 8:
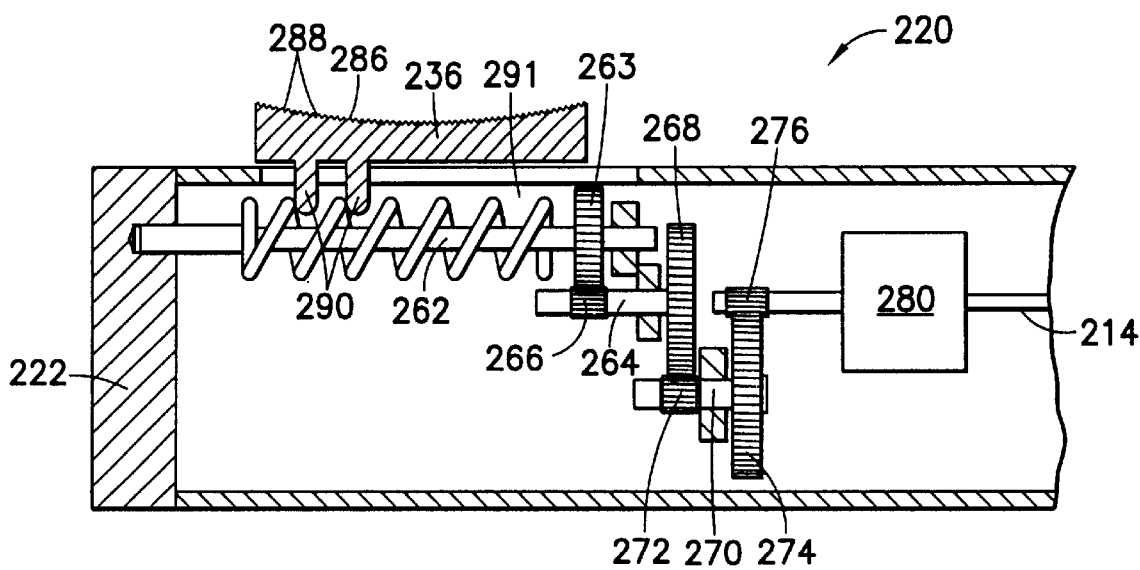
FIG. 8 is a broken side elevation section view of an alternate handle assembly according to the invention.
Figure 9:
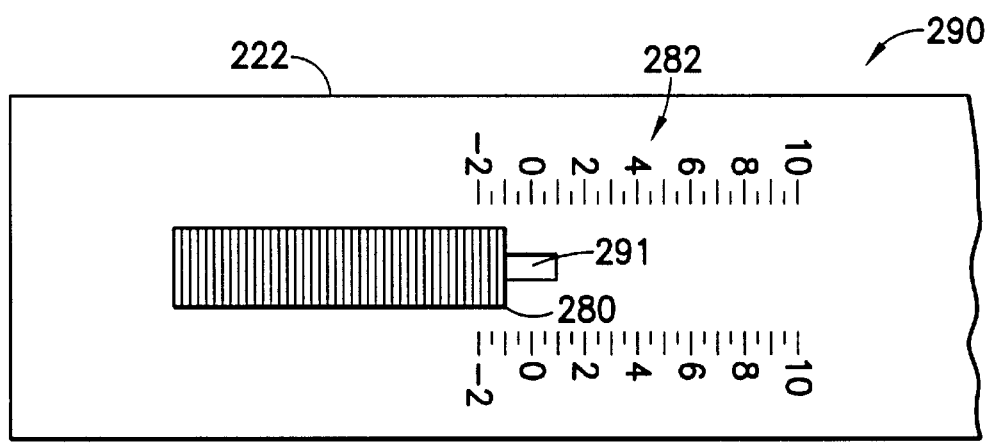
FIG. 9 is a broken top view of the alternate handle assembly of FIG. 8.

Turning to FIGS. 8 and 9, the handle assembly of either embodiment of the endoscopic needle injection device may be provided with a step-up gear assembly which translates linear motion of a control member into rotational movement of the shaft. As such, the handle assembly 220 includes a housing 222 and a control member 236 slidable relative to the housing. The control member 236 includes an upper finger engageable portion 286 engageable by a finger of the operator of the device, preferably provided with ridges 288 or another high friction surface, and has a rack portion 290 extending partially through a slot 291 in the housing into the interior of the housing. If desired, the control member 236 can also include an indicator 280 which can be aligned relative to graduated indicia 282 on the housing 222 to indicate the position of the needle tip relative to the distal end of the sheath, as effectuated by movement of the control member 236 relative to the housing 222 described below. A gear assembly 260 includes a helically threaded pinion 262 which is engaged by the rack portion 290 such that longitudinal movement of the control member 236 relative to the housing 222 causes the rack portion to move against the thread of the pinion 262 and cause rotation of the pinion. The pinion 262 has an output wheel 263 which engages a pinion 266 of change gear 264. The change gear 264 has a gear-toothed output wheel 266 which engages a pinion 272 of an output gear 270, and the output gear 270 has a output wheel 274 which engages a pinion 276 coupled to an axially compliant assembly 280, described above. The gear assembly 260 operates to "step-up" rotation of the output wheel 274 relative to rotation of the pinion 262, as also described above. The amount of sliding movement of the control member 236 required to move the needle may be in a one to one ratio (i.e., movement of the control member 236 six millimeters relative to the housing 222 may result in axial movement of the needle six millimeters relative to the sheath), or the sliding movement may be in another ratio (e.g., two to one or three to one). Such movement is determined by the selection of the relative ratio of the gear teeth on the gears of the gear assembly, as discussed above. Regardless of the particular gear ratio, the gear assembly effectuates appropriate rotation of the through the axially compliant assembly 280, such that a predetermined and reasonable sliding movement of the control member 236 relative to the housing 222 effectuates accurate, precise, and sufficient movement of the needle relative to the sheath at the distal end of the device.

There have been described and illustrated herein embodiments of an endoscopic needle injection device. While particular embodiments of the invention have been described, it is not intended that the invention be limited thereto, as it is intended that the invention be as broad in scope as the art will allow and that the specification be read likewise. Thus, while a particular handle assembly has been disclosed, it will be appreciated that other handle assemblies can be used as well. For example, instead of utilizing a built-in syringe port, a "T" or "Y" connector could be provided at the proximal end of the device, preferably built into the handle, so that a flexible extension tube could extend from the device to a separate syringe for injecting fluid through the device. Such a "T" or "Y" connector, in its simplest form, has a distal end which connects to the sheath, a proximal end which incorporates a fluid seal which allows the shaft to rotate and translate through the fluid seal, and a side port which connects directly or by means of an extension hose to the syringe. In addition, while stops are shown adjacent the threaded connection of the needle sleeve and sheath sleeve, one or more stops may additionally or alternatively be provided at the control knob to prevent rotation of the control knob beyond a predetermined location, thereby limiting extension and retraction of the needle. Also, while in the second embodiment the needle sleeve is shown about the needle, it may alternatively be provided about the inner tubular member. Moreover, while in the second embodiment the shaft is shown coupled to the needle, the shaft may alternatively be coupled to the distal end of the inner tubular member. Furthermore, while particular types of gear boxes have been disclosed, it will be understood that gears with other numbers of gear teeth, and other relative ratios, can be used. Furthermore, while one gear assembly capable of transferring linear movement of a sliding control member into rotational movement of the shaft is shown, other gear assemblies, e.g., using bevel gears or an alternate rack and pinion gear, may be used. In addition, while the relative position of the needle relative to the sheath is indicated by the alignment of indicia, it will be appreciated that their relative positions may be indicated through a mechanical indicator operated by the gear assembly. Also, while one sliding assembly has been disclosed, it will be appreciated that other sliding components may be utilized. For example, the shaft may be provided with a tubular member having a non-circular bore, and the output end of the pinion may be non-circular and slidable within the non-circular bore. Furthermore, while square-shaped and hex-shaped keys have been disclosed for over the proximal end of the shaft, keys having other shapes may be used. Moreover, it is not necessary that the key on the shaft and bore on the end of the output end of the pinion have the same shape; only that they have interfering cross-sectional shapes. Also, while a stainless steel wire shaft has been disclosed, other torque transmitting shaft constructs and materials may be used. In addition, while axial needle movement of between ten to twelve millimeters is preferred, the device may be adapted to permit greater or lesser needle movement. Furthermore, while a seal is shown at the distal end of the device including an O-ring sealing against the threads of the sheath sleeve, other types of seals, at the sheath sleeve or elsewhere, may be used, so long as the seal is effective to prevent substantial leakage of fluid at the distal end of the device. For example, an O-ring may be provided proximal or distal the sheath sleeve, positioned against a relatively smooth inner surface of the sheath. It will therefore be appreciated by those skilled in the art that yet other modifications could be made to the provided invention without deviating from its spirit and scope as claimed.

What is claimed is:

1. A needle injection device, comprising:
    a) a flexible sheath having proximal and distal ends and provided with first threads at said distal end of said sheath;
    b) a flexible shaft having proximal and distal ends and extending through the sheath;
    c) a needle having a bore in fluid communication with said sheath, said needle being coupled to said distal end of said shaft and provided with second threads threadably mated with said first threads and helically movable relative thereto; and
    d) a handle assembly including,
        i) a stationary member coupled to said sheath,
        ii) a control member movable relative to said stationary member,
        iii) an input gear, and
        iv) a step-up gear assembly coupled between said input gear and said shaft, said step-up gear assembly configured such that movement of said control member relative to said stationary member causes rotation of said input gear coupled to said control member by a first degree and rotation of said shaft by a second degree greater than said first degree.

2. A needle injection device according to claim 1, wherein:
said control member is rotatable relative to said stationary member.

3. A needle injection device according to claim 2, wherein:
rotation of said control member relative to said stationary member by a first degree causes rotation of said shaft by a second degree greater than said first degree.

4. A needle injection device according to claim 3, wherein:
said second degree is 12 to 100 times said first degree.

5. A needle injection device according to claim 1, wherein:
said device has an axis, and said control member is movable parallel to said axis.

6. A needle injection device according to claim 5, wherein:
said control member includes a rack portion which engages a pinion of said gear assembly such that movement of said control member relative to said pinion causes said shaft to rotate relative to said sheath.

7. A needle injection device according to claim 1, wherein:
said gear assembly includes an output pinion which is slidably coupled to said proximal end of said shaft.

8. A needle injection device according to claim 7, wherein:
said output pinion includes one of a bore having a non-circular cross-section and a key portion having a non-circular cross-section, and said proximal end of said shaft includes the other of said bore having said non-circular cross-section and said key portion having said non-circular cross-section, said key portion being slidably movable within said bore yet rotationally interfering with said bore.

9. A needle injection device according to claim 1, wherein:
said handle assembly includes means for indicating an axial position of said needle relative to said distal end of said sheath.

10. A needle injection device according to claim 9, wherein:
said means for indicating comprises indicia and at least one of said control member and said stationary member is provided with said indicia.

11. A needle injection device according to claim 1, wherein:
said stationary member includes a channel in fluid communication with said sheath, said channel terminating in a port.

12. A needle injection device according to claim 11, further comprising:
e) a syringe coupled to said port.

13. A needle injection device according to claim 1, wherein:
said shaft extends at least partially within said channel and proximally exits a medial portion of said channel through a substantially fluid-tight seal.

14. A needle injection device according to claim 1, wherein:
said internal threads provided to said sheath are included in a sleeve coupled within said sheath.

15. A needle injection device according to claim 1, wherein:
said external threads provided to said needle are included on a sleeve coupled over said needle.

16. A needle injection device according to claim 1, further comprising:
e) a fluid-seal between said needle and said distal end of said sheath.

17. A needle injection device according to claim 1, wherein:
said shaft is free of camber.

18. A needle injection device, comprising:
a) a flexible sheath having proximal and distal ends and provided with first threads at said distal end of said sheath;
b) a flexible shaft having proximal and distal ends and extending through the sheath;
c) a needle having a bore in fluid communication with said sheath, said needle being coupled to said distal end of said shaft and provided with second threads threadably mated with said first threads and helically movable relative thereto; and
d) a handle assembly including,
  i) a stationary member coupled to said sheath, and
  ii) a control member coupled to said shaft and rotatable relative to said stationary member,
  wherein rotation of said control member by no more than 360° relative to said stationary member causes said needle to move axially at least 2 mm relative to said sheath.

19. A needle injection device according to claim 18, wherein:
said wherein rotation of said control member by no more than 360° relative to said stationary member causes said needle to move axially at least 8 mm relative to said sheath.

20. A needle injection device, comprising:
a) a flexible sheath having an axis and proximal and distal ends and provided with first threads at said distal end of said sheath;
b) a flexible shaft having proximal and distal ends and extending through the sheath;
c) a needle having a bore in fluid communication with said sheath, said needle being coupled to said distal end of said shaft and provided with second threads threadably mated with said first threads and helically movable relative thereto; and
d) a handle assembly including,
  i) a stationary member coupled to said sheath, and
  ii) a control member coupled to said shaft and movable parallel to said axis of said sheath,
  wherein movement of said control member relative to said stationary member by a first amount causes said needle to move axially relative to said sheath by a second amount.

21. A needle injection device according to claim 20, wherein:
said first amount is more than said second amount.

22. A needle injection device according to claim 20, wherein:
said first amount is at least twice said second amount.

23. A needle injection device, comprising:
a) a sheath having proximal and distal ends and provided with first threads at said distal end of said sheath;
b) a flexible shaft having proximal and distal ends and extending through the sheath;

c) a needle having a bore in fluid communication with said sheath, said needle being coupled to said distal end of said shaft and provided with second threads threadably mated with said first threads and helically movable relative thereto; and d) a handle assembly including,
   i) a stationary member coupled to said sheath,
   ii) a control member movable relative to said stationary member and coupled to said shaft for rotating said shaft relative to said sheath, and
   iii) an indicator which indicates an axial position of said needle relative to said distal end of said sheath.

24. A needle injection device according to claim 23, wherein:

said handle assembly further includes a step-up gear assembly coupled between said control member and said shaft, said gear assembly configured such that rotation of said control member relative to said stationary member by a first degree causes rotation of said shaft by a second degree greater than said first degree.

25. A needle injection device according to claim 24, wherein:

said second degree is 12 to 100 times said first degree.

26. A needle injection device according to claim 24, wherein:

said gear assembly includes an output pinion which is slidably coupled to said proximal end of said shaft.

27. A needle injection device according to claim 26, wherein:

said output pinion includes one of a bore having a non-circular cross-section and a key portion having a non-circular cross-section, and said proximal end of said shaft includes the other of said bore having said non-circular cross-section and said key portion having said non-circular cross-section, said key portion being slidably movable within said bore yet rotationally interfering with said bore.

28. A needle injection device according to claim 23, wherein:

said control member includes a rack portion which engages a pinion coupled to said shaft, such that movement of said control member relative to said pinion causes said shaft to rotate relative to said sheath.

29. A needle injection device according to claim 23, wherein:

said stationary member includes a port in fluid communication with said sheath.

30. A needle injection device, comprising:

a) a sheath having proximal and distal ends and provided with first threads at said distal end of said sheath;

b) a flexible first shaft having proximal and distal ends and extending through the sheath;

c) a needle having a bore in fluid communication with said sheath, said needle being coupled to said distal end of said shaft and provided with second threads threadably mated with said first threads and helically movable relative thereto; and d) a handle assembly including,
   i) a stationary member coupled to said sheath,
   ii) a control member movable relative to said stationary member, and
   iii) a rigid second shaft member coupled to said control member such that movement of said control member relative to said stationary member causes rotation of said rigid shaft member relative to said sheath, said rigid shaft member including one of a bore having a non-circular cross-section and a key portion having a non-circular cross-section, and said proximal end of said first shaft including the other of said bore having said non-circular cross-section and said key portion having said non-circular cross-section, said key portion being slidably movable within said bore yet rotationally interfering with said bore such that movement of said control member relative to said stationary member causes rotation of said first shaft.

31. A needle injection device according to claim 30, wherein:

said control member is rotatable relative to said stationary member and said handle assembly further includes a step-up gear assembly coupled between said control member and said rigid second shaft member, said gear assembly configured such that rotation of said control member relative to said stationary member by a first degree causes rotation of said first shaft by a second degree greater than said first degree.

32. A needle injection device, comprising:

a) a flexible sheath having proximal and distal ends and provided with first threads at said distal end thereof;

b) a flexible inner tubular member having proximal and distal ends and extending through the sheath;

c) a needle coupled to said distal end of said inner tubular member, said needle having a bore in fluid communication with said inner tubular member, said needle being provided with second threads threadably mated with said first threads and helically movable relative thereto;

d) a flexible shaft having proximal and distal ends, said distal end of said flexible shaft coupled to one of said needle and said distal end of said flexible inner tubular member; and e) a handle assembly including,
   i) a stationary member coupled to said sheath,
   ii) a control member rotatable relative to said stationary member, and
   iii) a step-up gear assembly coupled between said control member and said shaft, said gear assembly configured such that rotation of said control member relative to said stationary member by a first degree causes rotation of said shaft by a second degree greater than said first degree.

33. A needle injection device according to claim 32, wherein:

said second degree is 12 to 100 times said first degree.

34. A needle injection device according to claim 32, wherein:

said gear assembly includes an output pinion which is slidably coupled to said proximal end of said shaft, thereby permitting said shaft to move axially relative to said output pinion.

35. A needle injection device according to claim 34, wherein:

said output pinion includes one of a bore having a non-circular cross-section and a key portion having a non-circular cross-section, and said proximal end of said shaft includes the other of said bore having said non-circular cross-section and said key portion having said non-circular cross-section, said key portion being slidably movable within said bore yet rotationally interfering with said bore.

36. A needle injection device according to claim 34, wherein:

when said shaft slidably moves axially relative to said output pinion by a first distance, said inner tubular member is adapted to move axially relative to said sheath by said first distance.

37. A needle injection device according to claim 32, wherein:
said proximal end of said sheath is axially slidably within said housing.

38. A needle injection device according to claim 32, wherein:
said handle assembly indicates an axial position of said needle relative to said distal end of said sheath.

39. A needle injection device according to claim 38, wherein:
at least one of said control member and said stationary member are provided with indicia indicating an axial position of said needle relative to said distal end of said sheath.

40. A needle injection device according to claim 32, wherein:
said stationary member includes a channel in flu id communication with said sheath, said channel terminating in a port.

41. A needle injection device according to claim 40, further comprising:
e) a syringe coupled to said port.

42. A needle injection device, comprising:
a) a flexible sheath having proximal and distal ends and provided with first threads at said distal end thereof;
b) a flexible inner tubular member having proximal and distal ends and extending through the sheath;
c) a needle coupled to said distal end of said inner tubular member, said needle having a bore in fluid communication with said inner tubular member, said needle being provided with second threads threadably mated with said first threads and helically movable relative thereto;
d) a flexible shaft having proximal and distal ends, said distal end of said flexible shaft coupled to one of said needle and said distal end of said flexible inner tubular member; and
e) a handle assembly including,
   i) a stationary member coupled to said sheath, and
   ii) a control member coupled to said shaft and rotatable relative to said stationary member,
   wherein rotation of said control member by no more than 360° relative to said stationary member causes said needle to move axially at least 2 mm relative to said sheath.

43. A needle injection device according to claim 42, wherein:
rotation of said control member by no more than 360° relative to said stationary member causes said needle to move axially at least 6 mm relative to said sheath.

44. A needle injection device, comprising:
a) a flexible sheath having proximal and distal ends and provided with first threads at said distal end thereof;
b) a flexible inner tubular member having proximal and distal ends and extending through the sheath;
c) a needle coupled to said distal end of said inner tubular member, said needle having a bore in fluid communication with said inner tubular member, said needle being provided with second threads threadably mated with said first threads and helically movable relative thereto;
d) a flexible shaft having proximal and distal ends, said distal end of said flexible shaft coupled to one of said needle and said distal end of said flexible inner tubular member; and
e) a handle assembly including,
   i) a stationary member coupled to said sheath,
   ii) a control member movable relative to said stationary member and coupled to said shaft for rotating said shaft relative to said sheath, and
   iii) an indicator which indicates an axial position of said needle relative to said distal end of said sheath.

45. A needle injection device, comprising:
a) a flexible sheath having proximal and distal ends and provided with first threads at said distal end thereof;
b) a flexible inner tubular member having proximal and distal ends and extending through the sheath;
c) a needle coupled to said distal end of said inner tubular member, said needle having a bore in fluid communication with said inner tubular member, said needle being provided with second threads threadably mated with said first threads and helically movable relative thereto;
d) a flexible first shaft having proximal and distal ends, said distal end of said flexible shaft coupled to one of said needle and said distal end of said flexible inner tubular member; and
e) a handle assembly including,
   i) a stationary member coupled to said sheath,
   ii) a control member movable relative to said stationary member, and
   iii) a rigid second shaft member coupled to said control member such that movement of said control member relative to said stationary member causes rotation of said second shaft member relative to said sheath, said second shaft member including one of a bore having a non-circular cross-section and a key portion having a non-circular cross-section, and said proximal end of said first shaft including the other of said bore having said non-circular cross-section and said key portion having said non-circular cross-section, said key portion being slidably movable within said bore yet rotationally interfering with said bore such that rotation of said control member causes rotation of said first shaft.

46. A needle injection device according to claim 45, wherein:
said handle assembly further includes a step-up gear assembly coupled between said control member and said first shaft, wherein said second shaft member is an output pinion of said gear assembly, said gear assembly configured such that rotation of said control member relative to said stationary member by a first degree causes rotation of said first shaft by a second degree greater than said first degree.

47. A needle injection device, comprising:
a) a flexible sheath having proximal and distal ends and provided with first threads at said distal end of said sheath;
b) a flexible shaft having proximal and distal ends and extending through the sheath;
c) a needle having a bore in fluid communication with said sheath, said needle being coupled to said distal end of said shaft and provided with second threads threadably mated with said first threads and helically movable relative thereto; and d) a handle assembly including,
   i) a stationary member coupled to said sheath,
   ii) a control member having a rack portion and movable relative to said stationary member, and
   iii) a gear assembly coupled between said control member and said shaft, said gear assembly including a pinion engaged by said rack portion of said control member such that movement of said control member relative to said pinion causes rotation of said pinion.

48. A needle injection device according to claim 47, wherein:

said device has an axis, and said control member is movable substantially parallel to said axis.

49. A needle injection device according to claim 47, wherein:

said gear assembly includes at least one change gear between said pinion and said shaft such that rotation of said pinion by a first degree causes rotation of said shaft by a second degree greater than said first degree.

* * * * *